(12) United States Patent
List et al.

(10) Patent No.: US 7,223,276 B2
(45) Date of Patent: May 29, 2007

(54) BLOOD REMOVAL SYSTEM

(75) Inventors: Hans List, Hesseneck-Kailbach (DE); Peter Ruschke, Budenheim (DE); Bruno Robert Thoes, Quierschied (DE); Hans Kintzig, Tiefenthal (DE); Michael Schabbach, Weinheim (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 617 days.

(21) Appl. No.: 10/445,606

(22) Filed: May 27, 2003

(65) Prior Publication Data
US 2004/0092996 A1    May 13, 2004

(30) Foreign Application Priority Data
May 28, 2002  (DE) ................. 102 23 558

(51) Int. Cl.
*A61B 17/32* (2006.01)
(52) U.S. Cl. ..................................... 606/181
(58) Field of Classification Search ............ 606/1, 606/181, 182; 600/583; 504/207
See application file for complete search history.

(56) References Cited

U.S. PATENT DOCUMENTS

| | | | |
|---|---|---|---|
| 3,030,959 A | 4/1962 | Grunert |
| 3,244,317 A | 4/1966 | Raybin |
| 3,696,915 A | 10/1972 | Douglas |
| 3,833,146 A | 9/1974 | Braginetz |
| 4,139,011 A | 2/1979 | Benoit et al. |
| 4,203,446 A | 5/1980 | Höfert et al. |
| 4,388,925 A | 6/1983 | Burns |
| 4,416,279 A | 11/1983 | Lindner et al. |
| 4,442,836 A | 4/1984 | Meinecke et al. |
| 4,449,529 A | 5/1984 | Burns et al. |
| 4,469,110 A | 9/1984 | Slama |
| 4,527,561 A | 7/1985 | Burns |
| 4,535,769 A | 8/1985 | Burns |
| 4,539,988 A | 9/1985 | Shirley et al. |
| 4,553,541 A | 11/1985 | Burns |
| 4,577,630 A | 3/1986 | Nitzsche et al. |
| 4,624,253 A | 11/1986 | Burns |
| 4,635,633 A | 1/1987 | Hufnagle |
| 4,653,513 A | 3/1987 | Dombrowski |
| 4,677,979 A | 7/1987 | Burns |
| 4,712,548 A | 12/1987 | Enstrom |
| 4,715,374 A | 12/1987 | Maggio |
| 4,735,203 A | 4/1988 | Ryder et al. |
| 4,738,261 A | 4/1988 | Enstrom |

(Continued)

FOREIGN PATENT DOCUMENTS

DE    2 803 345 B1    6/1979

(Continued)

*Primary Examiner*—Anhtuan T. Nguyen
*Assistant Examiner*—Tuan Van Nguyen
(74) *Attorney, Agent, or Firm*—Bose McKinney & Evans LLP (57) ABSTRACT

Blood removal system for removing blood for diagnostic purposes including a housing, a lancet guide, and a lancet drive with a drive spring. The lancet drive comprises a cocking device, in order to tension the drive spring, a drive rotor that is driven by the drive spring, and an output-side coupling mechanism, by means of which the rotational movement of the drive rotor is converted into the puncturing movement.

64 Claims, 4 Drawing Sheets

U.S. PATENT DOCUMENTS

| | | |
|---|---|---|
| 4,794,926 A | 1/1989 | Munsch et al. |
| 4,817,603 A | 4/1989 | Turner et al. |
| 4,821,878 A | 4/1989 | Jones |
| 4,844,095 A | 7/1989 | Chiodo et al. |
| 4,856,515 A | 8/1989 | Turner et al. |
| 4,858,607 A | 8/1989 | Jordan et al. |
| 4,860,937 A | 8/1989 | Arnold |
| 4,869,249 A | 9/1989 | Crossman et al. |
| 4,889,117 A | 12/1989 | Stevens |
| 4,892,097 A | 1/1990 | Ranalletta et al. |
| 4,895,147 A | 1/1990 | Bodicky et al. |
| 4,924,879 A | 5/1990 | O'Brien |
| 4,976,724 A | 12/1990 | Nieto et al. |
| 4,983,178 A | 1/1991 | Schnell |
| 4,990,154 A | 2/1991 | Brown et al. |
| 4,994,068 A | 2/1991 | Hufnagle |
| 4,995,402 A | 2/1991 | Smith et al. |
| 4,998,452 A | 3/1991 | Blum |
| 5,026,388 A | 6/1991 | Ingalz |
| 5,029,583 A | 7/1991 | Meserol et al. |
| 5,035,704 A | 7/1991 | Lambert et al. |
| 5,047,044 A | 9/1991 | Smith et al. |
| 5,070,886 A | 12/1991 | Mitchen et al. |
| 5,074,872 A | 12/1991 | Brown et al. |
| 5,100,427 A | 3/1992 | Crossman et al. |
| 5,100,428 A | 3/1992 | Mumford |
| 5,105,823 A | 4/1992 | Blum |
| 5,120,311 A | 6/1992 | Sagstetter et al. |
| 5,133,730 A | 7/1992 | Biro et al. |
| 5,147,375 A | 9/1992 | Sullivan et al. |
| 5,152,775 A | 10/1992 | Ruppert |
| 5,196,025 A | 3/1993 | Ranalleta et al. |
| 5,207,699 A | 5/1993 | Coe |
| 5,269,800 A | 12/1993 | Davis, Jr. |
| 5,304,192 A | 4/1994 | Crouse |
| 5,304,193 A | 4/1994 | Zhadanov |
| 5,314,442 A | 5/1994 | Morita |
| 5,318,584 A * | 6/1994 | Lange et al. ................ 606/182 |
| 5,356,420 A | 10/1994 | Czernecki et al. |
| 5,366,470 A | 11/1994 | Ramel |
| 5,397,334 A | 3/1995 | Schenk et al. |
| 5,439,473 A | 8/1995 | Jorgensen |
| 5,464,418 A | 11/1995 | Schraga |
| 5,478,345 A | 12/1995 | Stone et al. |
| 5,487,748 A | 1/1996 | Marshall et al. |
| 5,514,152 A | 5/1996 | Smith |
| 5,527,334 A | 6/1996 | Kanner et al. |
| 5,531,763 A | 7/1996 | Mastri et al. |
| 5,554,166 A | 9/1996 | Lange et al. |
| 5,628,765 A | 5/1997 | Morita |
| 5,632,410 A | 5/1997 | Moulton et al. |
| 5,636,640 A | 6/1997 | Staehlin |
| 5,643,306 A | 7/1997 | Schraga |
| 5,662,669 A | 9/1997 | Abidin et al. |
| 5,755,733 A | 5/1998 | Morita |
| 5,829,589 A | 11/1998 | Nguyen et al. |
| 5,908,434 A | 6/1999 | Schraga |
| 5,951,582 A | 9/1999 | Thorne et al. |
| 5,984,940 A | 11/1999 | Davis et al. |
| 6,056,765 A | 5/2000 | Bajaj et al. |
| 6,109,740 A * | 8/2000 | Namekawa et al. .......... 347/85 |
| 6,358,265 B1 | 3/2002 | Thorne, Jr. et al. |
| 6,409,740 B1 | 6/2002 | Kuhr et al. |
| 6,419,661 B1 | 7/2002 | Kuhr et al. |
| 6,472,220 B1 | 10/2002 | Simons et al. |
| 6,514,270 B1 | 2/2003 | Schraga |
| 6,719,771 B1 | 4/2004 | Crossman |
| 2003/0050656 A1 | 3/2003 | Schraga |
| 2004/0039407 A1 | 2/2004 | Schraga |
| 2004/0127928 A1* | 7/2004 | Whitson et al. ............ 606/181 |
| 2005/0090850 A1* | 4/2005 | Thoes et al. ................ 606/182 |
| 2005/0131441 A1* | 6/2005 | Iio et al. .................... 606/182 |

FOREIGN PATENT DOCUMENTS

| | | |
|---|---|---|
| DE | 38 42 317 A1 | 6/1990 |
| DE | G 92 05 278.9 | 8/1992 |
| EP | 0 036 443 B1 | 3/1986 |
| EP | 0 081 665 B1 | 4/1986 |
| EP | 0 204 892 B1 | 1/1991 |
| EP | 0 178 384 B1 | 11/1991 |
| EP | 0 199 484 B1 | 3/1993 |
| EP | 0 565 970 A1 | 10/1993 |
| EP | 0 589 186 A1 | 3/1994 |
| EP | 0 582 226 B1 | 10/1997 |
| EP | 0 931 507 | 7/1999 |
| FR | 2 508 305 | 12/1982 |
| GB | 1085141 | 9/1967 |
| JP | 2002143131 * | 5/2002 |
| WO | WO 85/04089 | 9/1985 |
| WO | WO 93/00044 | 1/1993 |
| WO | WO 96/02189 A1 | 2/1996 |
| WO | WO 98/14125 | 4/1998 |
| WO | WO 01/00090 A1 | 1/2001 |
| WO | WO 02/36010 A1 | 5/2002 |

* cited by examiner

BLOOD REMOVAL SYSTEM

FIELD OF THE INVENTION

The invention refers to a blood removal system for withdrawing blood for diagnostic purposes.

BACKGROUND OF THE INVENTION

In order to withdraw a minimal amount of blood from body parts (generally, a finger or an ear lobe) for analytical-diagnostic purposes, lancets are used, which are pricked into the corresponding body part for producing a wound. Because this procedure is manually performed, specially trained personnel are necessary. However, the puncture is connected with substantial pain.

Blood removal systems which comprise a pricking apparatus and associated lancets, specially adapted to the lancets, have also been used. In a housing of the pricking apparatus, a lancet drive is located, by means of which a lancet is mechanically stuck into the skin. A spring serves as a driving element for the puncturing movement. At the beginning of the development, very simple constructions were used, in which the lancet was directly attached to an end of a compression spring arranged in an elongated housing (for example, U.S. Pat. No. 4,469,110).

These types of blood removal system were, however, not suitable to meet the high demands required when a routine monitoring of analytical values of blood is necessary. This is particularly true for diabetics, who must control their blood sugar levels frequently, in order to maintain their blood sugar levels as constant as possible within predetermined nominal limits by means of adapting insulin injections to the requirements (which, depending on the nutrient absorption, the bodily activity, etc., can vary strongly). By comprehensive scientific research, it was demonstrated that by means of an intensive therapy with at least four blood analyses per day, a dramatic decrease of the most severe consequences of diabetes mellitus (for example, a retinal pathology with resulting blindness of the patient) can be achieved.

This intensive therapy requires that the blood removal is connected with the least possible pain. Numerous different blood removal systems were developed with the aim to achieve this goal.

A blood removal with very little pain is achieved by blood removal systems, whose lancet drive includes a drive rotor, which on one side (the input side) is coupled with the drive spring in such a manner that it can be driven thereby to rotate about an axis of rotation. On the other side (output side) it is coupled via a coupling mechanism with the lancet, in such a manner that the rotation of the drive rotor resulting from the tension releasing movement of the drive spring is converted to a puncturing movement whereby the lancet is moved with high speed, until its point or tip exits from the exit opening, thereby producing a wound in the body part which is pressed against a contact surface surrounding the exit opening. The lancet is guided by a lancet guide on a predetermined (in practice, straight) puncture path.

A blood lancet device with such a rotor drive is described in U.S. Pat. No. 4,924,879. Its rotor is driven by means of a coaxial helical spring. The rotational movement of the rotor is converted into the required linear movement of the lancet via a con-rod drive.

In U.S. Pat. No. 5,318,584, a blood removal system is described, which, likewise, operates with a rotor drive. The drive rotor of this system rotates about an axis of rotation, which coincides with the axis of the longitudinally extending, "pencil-shaped" apparatus. A rotational spring that is coaxial with the rotor serves as the drive. The output-side coupling mechanism for converting the rotational movement into the translation movement of the lancet is formed by a curve controller. The form of the control curve makes it possible to cock the apparatus, without the lancet tip exiting from the housing. The rotation of the rotor part about the longitudinal axis of the apparatus leads to very little vibration and stabilizes the puncturing process. A newer version of a blood removal system with a drive rotor that rotates about the apparatus longitudinal axis is described in EP 1034740 A1.

A further embodiment of a rotor drive is described in EP 1090584 A2, in which a drive rotor is used, which rotates about an axis that runs transverse to the direction of puncture. Here the rotation of the drive rotor is caused by the force of the drive spring pressing against a specially formed pressure surface of the rotor. In this manner, it is possible that the rotor rotates in the same direction of rotation both during cocking as well as upon tension release of the lancet drive. Also in this case, the output-side coupling mechanism preferably comprises a curve controller. The construction requires fewer components than the previously discussed rotor drive. It requires, however, a relatively wide housing shape, which is considered less favorable by many users.

In spite of the extensive development work, which has led to the previously discussed and numerous further designs, a large interest exists in a blood removal system, which, at the same time, fulfills, to the extent possible, the difficult and partially opposing requirements (minimal pain, simple operation, compact, most slim structure, and simple, cost-effective construction).

SUMMARY OF THE INVENTION

To fulfill these requirements, the present invention is based on a blood removal system with a rotor drive. In this respect, in particular with regard to the required output-side coupling mechanism for conversion of the rotational movement of the drive rotor into the translation movement of the lancet, reference is made to the previously discussed documents. The disclosure of these documents is incorporated herein by reference. Based on this basic design the present invention proposes that the end of the drive spring facing away from the drive rotor is connected to a rotatably moveable cocking element, the cocking element is rotatable for tensioning of the drive spring, with inhibited rotation of the drive rotor, in the same direction of rotation in which the drive rotor rotates during the driving phase and that the cocking element is arrested during the drive phase against a backward rotation, so that the drive rotor, after releasing the rotation inhibition, performs a rotational movement, which, by means of the output-side coupling mechanism, is converted into the puncturing movement of the lancet.

With the earlier known rotor drives it was general practice that the drive spring (and thereby the entire rotor drive) was brought into the cocked state by turning the drive rotor backwards (i.e., in a rotation direction contrary to its direction during the puncturing movement). EP 1090584 A2 shows an exception, in which the specially formed pressure surface has alternating driving sections and tensioning sections in such a manner that the drive spring is tensioned via unidirectional rotation of the drive rotor when in the tensioning phase of the rotor drive, it is in contact with the tensioning section of the pressure surface, while in the driving phase of the drive the spring is in contact with a driving section of the rotor, whereby the rotational movement is driven by the relaxing spring.

According to the invention, the rotationally moveable cocking element and the drive rotor are alternately rotated in the same direction of rotation:

During the cocking phase, the cocking element is rotated, while simultaneously, the rotation of the drive rotor is inhibited.

During the driving phase, the cocking element is fixed against a reverse rotation, so that the drive rotor, after termination of the inhibition, can perform a rotational movement, which is converted by means of the output-side coupling mechanism into a corresponding translation movement of the lancet.

This principle is subsequently designated as "One Way Alternating Drive and Cocking", or OWADAC.

In one embodiment of the invention, the drive spring is connected directly, without further intermediary components, on one side to the drive rotor, and on the other side, directly to the cocking element. This configuration may require fewer components and provide reduced friction, in particular, when, according to another embodiment of the present invention, the axis of rotation of the cocking element runs coaxial to the axis of rotation of the drive rotor. In principle, it is also possible that the rotational axes of the cocking element and the drive rotor are parallel, but not coaxial, or that they even run at an angle to one another that is different from 0°. In this case, in particular, the connection of the drive spring relative to the drive rotor and/or the cocking element may be indirect, that is, further components (for example, gears or other drive parts) are provided, which permit the required conversion of the flow of force. Thus the statement that the spring is "connected to" or "supported against" the cocking element and the drive rotor is to be understood in the general sense that a force transfer between the cocking element, the drive spring and the drive rotor is provided, by means of which the rotation of the cocking element with a fixed drive rotor leads to tensioning of the drive spring and, with a fixed cocking element, the detensioning of the previously biased spring drives the drive rotor while the cocking element is fixed.

The invention will be described hereafter in greater detail with reference to the embodiments shown in the figures. The characteristics shown therein can be used individually or in combination, to provide preferred embodiments of the invention. In the figures:

DETAILED DESCRIPTION OF EMBODIMENTS OF THE INVENTION

The embodiments described below are merely exemplary and are not intended to limit the invention to the precise forms disclosed. Instead, the embodiments were selected for description to enable one of ordinary skill in the art to practice the invention.

Figure 1:
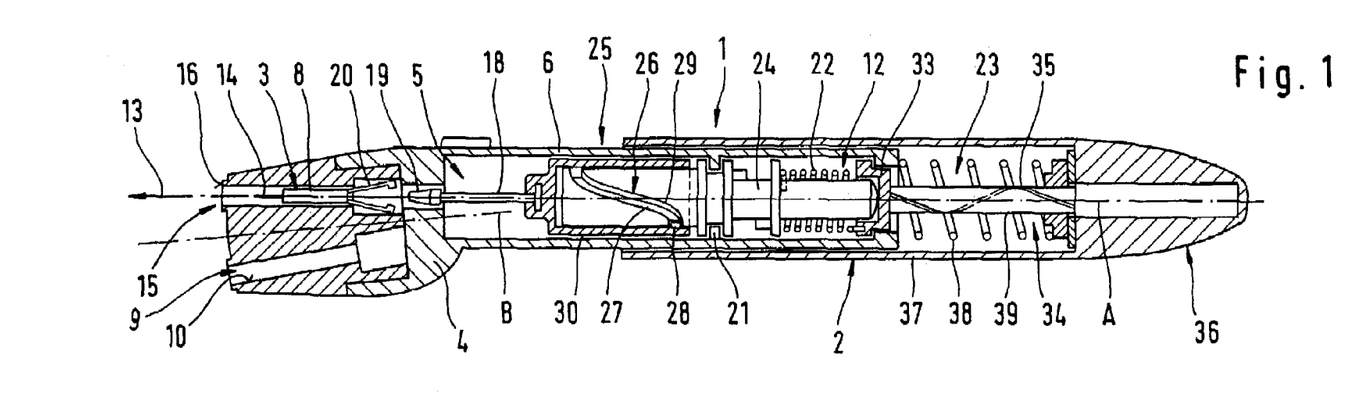
FIG. 1 is a side view of a longitudinal section of a blood removal system according to the present invention.

The blood removal system 1 shown in FIG. 1 comprises a puncture apparatus 2 and lancets 3. In the shown embodiment the lancets 3 are held in a revolver head 4 which can be attached exchangeably on the forward end 5 of the puncture apparatus 2 as part of its housing 6.

The revolver head 4 is rotatable about an axis of rotation B to be positioned in a plurality of positions, in which, respectively, one lancet 3 is arranged coaxial with the main axis A of the puncture apparatus 2. The lancet bodies 8 and the recesses 9, in which the lancets 3 sit, are shaped relative to one another such that the walls of the recesses 9 form lancet guides 10, by means of which the respective lancet 3 is guided on a predetermined puncture path (here, along the main axis A).

In the housing 6 of the puncture apparatus 2, a lancet drive 12 is provided, which serves to move a lancet 3 with high speed in the puncturing direction 13, until its tip 14 protrudes from an exit opening 15, while the puncture apparatus 2 is pressed with a contact surface 16 surrounding the exit opening 15 against a body part (not shown). Thereby, a wound for removal of blood is produced in the body part.

Before the puncturing movement is initiated a respective lancet 3 must be coupled with the lancet drive 12. In the shown embodiment this is achieved by means of a connecting rod, designated as a pushrod 18. On the end of the pushrod 18 facing the lancet 3, a holding element 19 with larger cross-section is provided, which for coupling of a lancet is inserted into a corresponding holding device 20 of the lancet body 8. The holding device 20 is formed, such that it engages the holding element 19 of the pushrod 18 in cooperation with the shape of the recess 9, when the pushrod 18 is moved so far in the puncturing direction 13 that its front end contacts the lancet body and displaces the lancet 3 from the position shown in FIG. 1 into the puncturing position (to the left). In this manner, the lancet 3 is form-fittingly coupled to the lancet drive. Particular details and alternative embodiments of a suitable coupling mechanism are described in international patent application PCT/EP01/12527. The contents of this document are hereby expressly incorporated by reference into the present application.

In the embodiment shown, the lancet 3 is "directly guided", that is, it is located directly in a part of the housing 6 (in the present case, a magazine which contains a plurality of lancets) that forms the guide required during the puncturing movement. The embodiment of the lancet drive explained here is suited in particular for such directly guided, magazined lancets. However, it is also usable with the generally used indirect lancet guides, where the lancet drive is permanently coupled with a lancet holder, into which a new lancet is manually inserted for each blood withdrawal. During the puncture process, the lancet holder is guided by means of a housing part serving as a guide and thereby indirectly provides the required guide of the lancet on the puncturing path. This type of construction is described in the earlier publications cited above.

The lancet drive 12 comprises essentially a drive spring 22, a cocking device 23 for tensioning of the drive spring 22, and a drive rotor 24 that is driven by the drive spring 22 and is rotatable about axis A. The drive rotor 24 is secured against axial displacement by means of a bearing pin 21. By means of an output-side coupling mechanism 25, the rotational movement of the drive rotor 24 is converted into the puncturing movement which is by means of the pushrod 18 transferred to a lancet coupled thereon.

The output-side coupling mechanism 25 is in the shown device embodied as a curve controller with a control curve 27 and a control pin 28 travelling along the control curve 27 during the puncturing movement. In the shown embodiment, the control curve 27 is formed by a recess running about the periphery of the drive rotor 24. The control pin 28 is formed on a driving sleeve 30, which surrounds the part of the drive rotor 24 provided with the control curve 27. The driving sleeve 30 is non-rotatably guided by means of a longitudinal groove (not shown), such that it can only carry out a translation movement. At its front end, the pushrod 18 is rigidly fixed. The output-side coupling mechanism 25 is similar to the curve controllers described in U.S. Pat. No. 5,318,584 and in EP 1034740 A1. In the present invention, however, the drive rotor need not be reversely rotated during the tensioning of the drive spring 22. Therefore, on the one hand, a very simple form of the control curve 27 can be chosen, and on the other hand, the entire angle of rotation of 360° can be used for the conversion of the rotational movement of the drive rotor 24 into a translation movement of the pushrod 18 and a lancet 3 connected therewith.

This is achieved in that the cocking device 23 is designed according to the OWADAC principle. The end of the drive spring 22 facing away from the drive rotor 24 is connected to a rotationally movable cocking element 33, which, for tensioning of the drive spring 22 is rotatable in the same direction, in which the drive rotor 24 rotates during the driving phase, while the rotation of the drive rotor 24 is inhibited. During the driving phase, the cocking element 33 is arrested against a reverse rotation, so that the drive rotor 24, after release of its rotation-inhibiting state, performs the rotational movement. This again is converted into the puncturing movement of the lancet 3.

With the embodiment shown in FIG. 1, the rotationally movable cocking element 33 is connected via a rotary/sliding transmission 34, which in the shown case is again embodied by means of a control curve 35, with a translatory moveable actuator element 36, which projects from the housing 6. The actuator element 36 is, in the shown situation, formed by a sliding sleeve 37, which forms the rear part (with reference to the puncturing direction 13) of the housing 6. It can be displaced forward in the direction of the main axis A of the puncture apparatus 2 against the force of a return spring 38. The control curve 35 is formed in a shaft 39, which is nonrotatably connected with the cocking element 33. It is supported such that it can rotate together with the cocking element, however, cannot be axially displaced. The movement of the sliding sleeve 37 is converted into a rotational movement of the cocking element 33 by means of the control curve 35 and a control pin (not shown) that travels along this curve 35.

Figure 2:
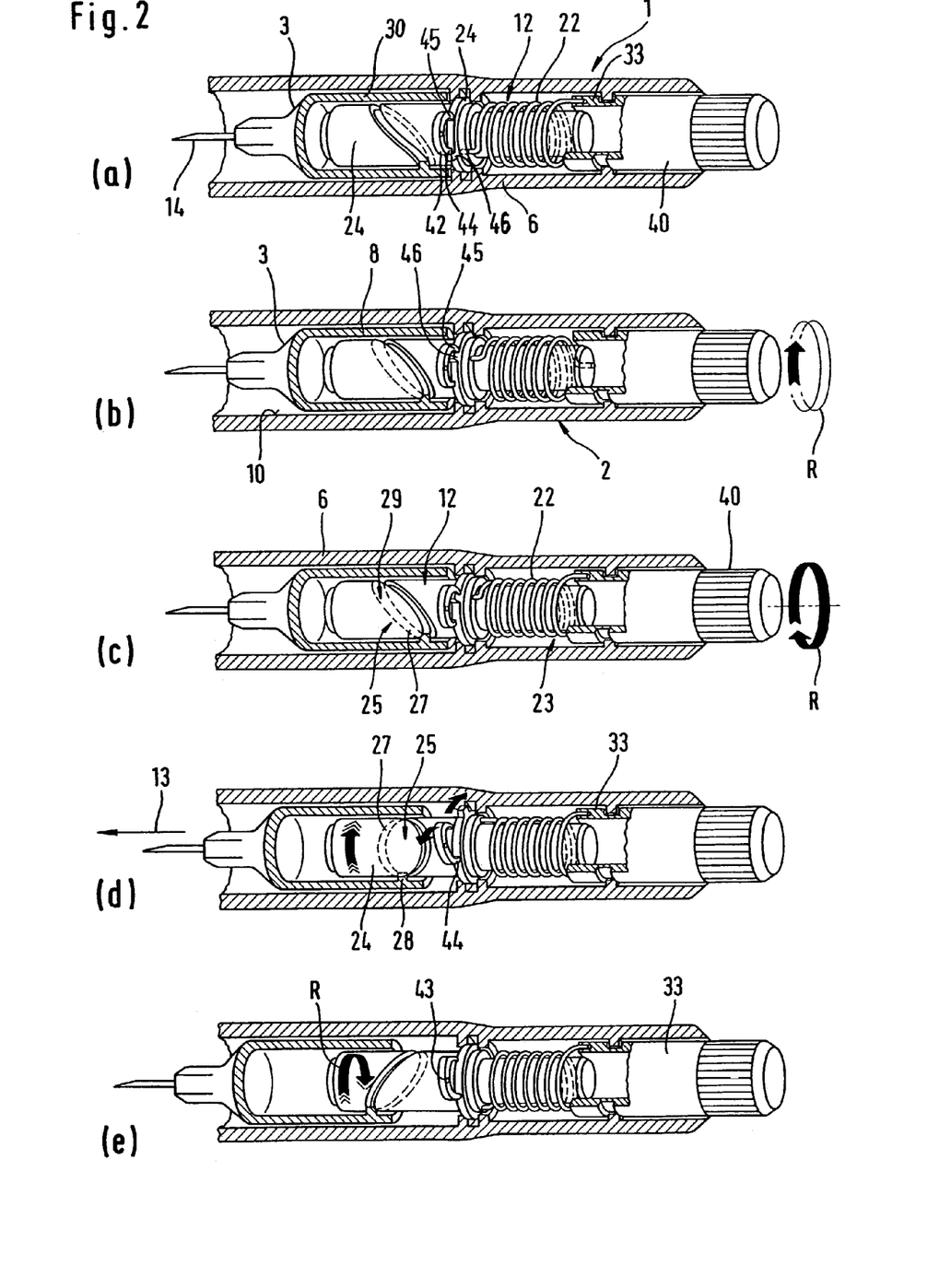
FIGS. 2a-2e are partially fragmented, perspective views of a blood removal system according to the present invention in five different movement positions or phases of the lancet drive.

Certain functions of the lancet drive 12 can be more clearly recognized with reference to FIG. 2. It shows an alternative embodiment of a blood removal system 1 according to the invention in five different movement phases. Functionally similar components are designated with the same reference numerals as used in FIG. 1. The following differences exist:

In order to simplify the drawing and to allow a good recognition of the functions of the invention, the mechanism for coupling exchangeable lancets is omitted. Instead, the blood removal system 1 shown in FIG. 2 has a lancet 3 rigidly connected with the driving sleeve 30.

For cocking of the lancet drive 12, a rotatable actuator element 40 is provided, which projects from the rear end of the housing 6. The actuator element 40 is fixedly connected to the cocking element 33.

In the embodiment shown a locking cam 42 is provided as a constructive element, by means of which the required stoppage of the rotation of the drive rotor during the cocking phase is achieved. By pivoting about an axis 43 it can be brought into two different positions, in which, respectively, one of two locking catches 44, 45 provided on its ends is located in a movement path of a stop element 46 provided on the drive rotor 24. The first locking catch, with reference to the rotational direction R of the drive rotor 24, is designated as the forward locking catch 44 and the second as the rear locking catch 45.

The movement position in FIG. 2a corresponds with the base state of the lancet drive 12. The drive spring 22 is relaxed. The stop element 46 rests against the forward locking catch 44 of the locking cam 42.

When the locking cam 42 is pivoted by means of an actuator element (not shown), into the position shown in FIG. 2b, the drive rotor 24 can rotate through an angle of rotation range, which corresponds to the distance between the forward locking catch 44 and the rear locking catch 45 of the locking cam 42. This range is designated as the "preparation angle of rotation range." This rotational movement of the drive rotor 24 is achieved by means of a corresponding rotation of the actuator element 40, by which a torque is directly transferred via the rotation spring 22 onto the drive rotor 24. If the drive spring 22 was completely relaxed in the base state (FIG. 2a), the components 40, 22, and 24 are commonly and uniformly rotated. If, in contrast, the drive spring 22 is in the base state (FIG. 2a) still under a residual tension, the movement in the preparation angle of rotation is partially or completely caused by the torque resulting from the residual tension of the drive spring 22. In each case, a slow rotational movement of the drive rotor 24 (in comparison to the puncture movement) results, which, by means of the output-side coupling mechanism 25 (here, the curve controller 26 formed by the control curve 27 and the control pin 28) is converted into a relatively slow movement of the lancet 3.

The movement of the lancet drive in the preparation angle of rotation range can be used for preparation of the actual puncture process. In particular, it can serve to couple the lancet drive with a lancet stored in a magazine. In particular, the coupling mechanism shown in FIG. 1 and specifically described in PCT/EP01/12527 can be used. The preparation angle of rotation range can, however, also be used advantageously for other purposes, for example, to bring a lancet holder into a position, in which a used lancet is ejected and the lancet holder is prepared for receiving a new lancet.

During the cocking phase shown in FIG. 2c, the stop element 46 rests on the rear locking catch 45. Therefore, the rotation of the drive rotor 24 in the direction of rotation R is inhibited. By rotating the actuator element 40 and the rotatably moveable cocking element 33 coupled therewith in the same direction of rotation R, the spring 22 is tensioned. At the end of the cocking movement, the cocking element 33 is locked by means of a locking mechanism not shown, such that, during the subsequent driving phase, it is arrested against a reverse rotation.

The driving phase of the lancet drive 12 shown in FIG. 2d is actuated by pivoting of the locking cam 42 into a position, in which its rear locking catch 45 releases the drive rotor 24, while its forward locking catch 44 is pivoted into the rotational path of stop element 46. After the release, the drive rotor 24 carries out a fast rotational movement, driven by the highly tensioned drive spring 22, which, by the output-side coupling mechanism 25, is converted into a precisely executed and fast (therefore low-pain) puncture- and return movement of the lancet.

FIG. 2e shows the position of the maximum penetration of the lancet 3, which corresponds with the lower reversal point of control curve 27. At the end of the puncture- and return movement, the rotational movement is stopped by the forward locking catch 44 of the locking cam 42, and the lancet drive is in the base state (FIG. 2a).

Figure 3:
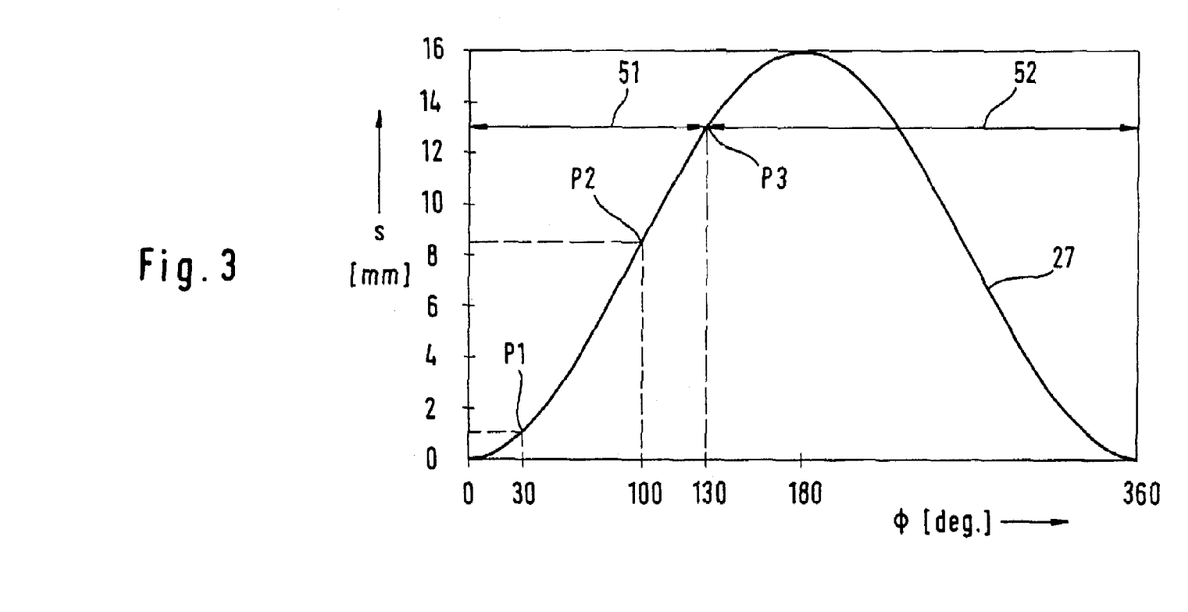
FIG. 3 is a graph of the dependency of the puncture depth on the angle of rotation of the drive rotor for explanation of the function of different angle of rotation ranges.
Figure 4:
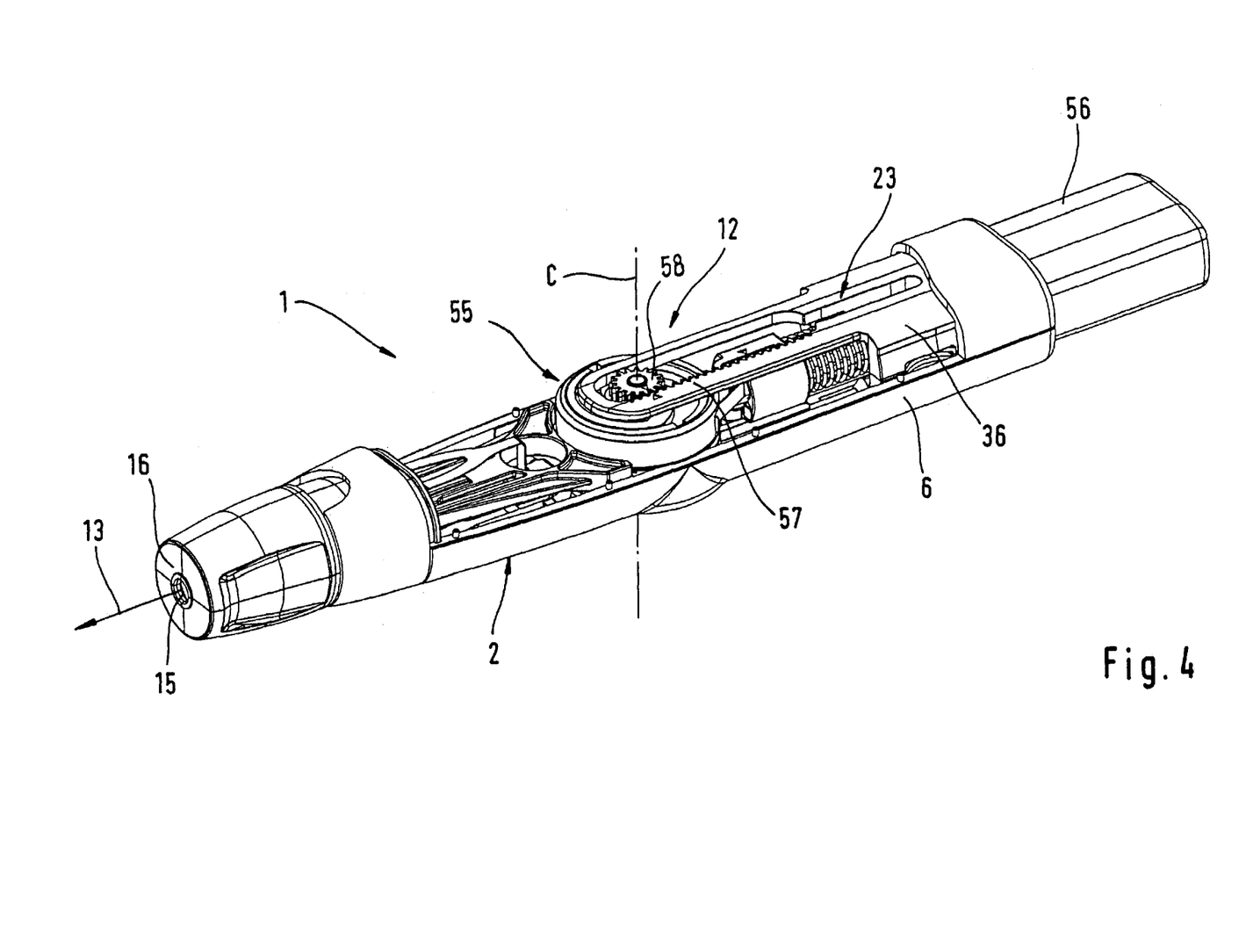
FIG. 4 is a partially fragmented, perspective view of a further embodiment of a blood removal system according to the present invention.
Figure 5:
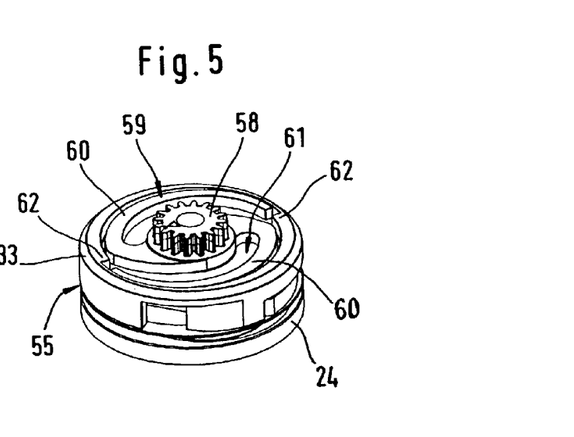
FIG. 5 is a perspective view of the drive module of the lancet drive used in the blood removal system of FIG. 4.
Figure 6:
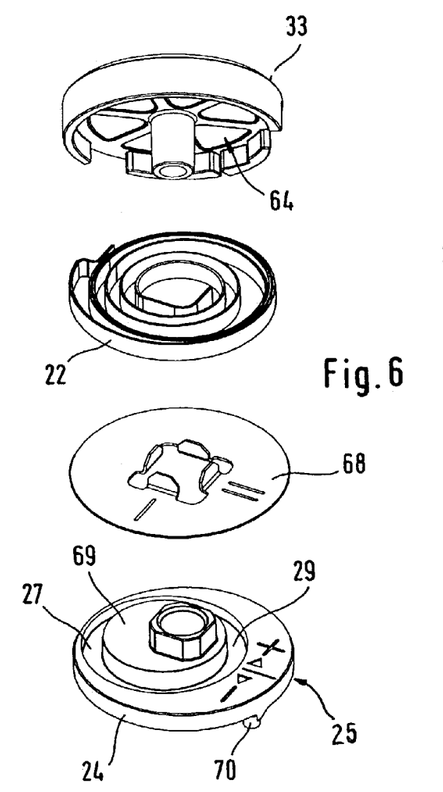
FIG. 6 is a perspective exploded view of components of the module of FIG. 5.
Figure 7:
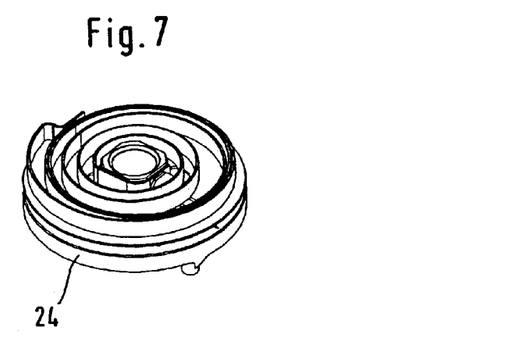
FIG. 7 is a perspective view of the module of FIG. 5 in a partially assembled state.
Figures 8, 9:
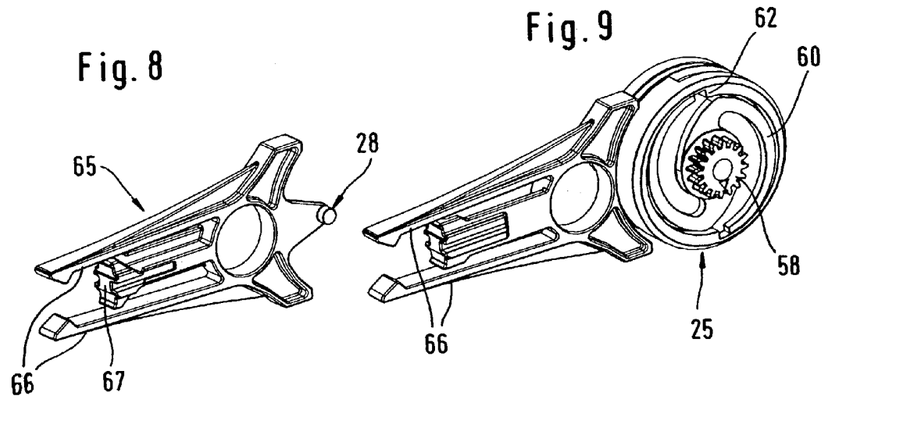
FIG. 8 is a perspective view of a lancet holder of the blood removal system of FIG. 4.
FIG. 9 is a perspective view of a subunit of the blood lancet system of FIG. 4 which is composed of a drive module according to FIG. 5 and a lancet holder according to FIG. 8.

FIG. 3 serves to explain in more detail how the described lancet drive can be used to realize different functions in two separate angle of rotation ranges. The shown sinus curve represents a development of a control curve 27 in the plane of the drawing. The entire angle of rotation range of the OWADAC drive (360°) is subdivided into a preparation angle of rotation range 51 (in the illustrated case, 130°) and into a puncture angle of rotation range 52 (230°).

In the initial section of the preparation angle of rotation range 51, the slope of the control curve 27 is small. This causes a slow movement with relative strong force. In the position P1 (in the case shown, at a puncture depth of 1 mm and an angle of 30°), a protective film covering the lancet receiving recesses 9 at the rear of the revolver head 4 is pierced by means of the front end of the pushrod 18 (FIG. 1). During further movement, the pushrod impinges the end of the lancet 3 at control curve position P2 (at 100° and approximately 8.5 mm movement path). The retaining element 19 of the pushrod 18 penetrates into the holding device 20 of the lancet 3, whereby the lancet 3 is coupled to the lancet drive 12. At the end of the preparation angle of rotation range 51 (FIG. 2b), the control pin 28 is located in position P3. After cocking and release of the inhibition, the drive rotor 24 rotates through the angle of rotation range 52, whereby the puncture and reverse movement proceeds.

The axis of the drive rotor runs parallel to the puncture direction (as shown in FIGS. 1 and 2). Alternatively, a drive rotor whose axis runs perpendicular to the puncture direction and the main axis of the puncture apparatus can be used. In this case, the output-side coupling mechanism 25, can, for example, be formed by a con-rod drive (see U.S. Pat. No. 4,924,879). The force transfer from an actuator element moving translatory in the puncture direction onto a rotatable cocking element that is coaxial to the drive rotor can take place, for example, by means of a gear rod and a pinion coupled with the cocking element.

Such an embodiment of a blood removal system 1 is shown in FIGS. 4 through 9. One element of the lancet drive 12 in this embodiment is a drive module 55. As shown, for example, in FIGS. 4 and 6, components of the drive module 55 are the drive rotor 24 and the rotatably moveable cocking element 33, which are rotatably about a common axis C running perpendicular to the puncture direction 13 and to the longitudinal axis of the puncture apparatus 2.

For cocking of the lancet drive 12, a translatory moving actuator element 36 is moved in the puncture direction by means of an actuator button 56. A gear rod 57 is a component of actuator element 36 and drives a pinion 58 that is coaxial to the cocking element 33. Pinion 58 is connected with cocking element 33 via a free wheel 59 (FIG. 5) in such a manner that both parts are coupled with one another during the cocking movement (movement of the actuator element 36 in the puncture direction), while being uncoupled during the return movement of the actuator element 36. In the embodiment shown, the free wheel 59 is realized by means of two elastic tongues 60, which are connected with the pinion 58. Tongues 60 are located in a recess 61 of cocking element 33 facing away from drive rotor 24. The recess 61 includes stops 62, on which the ends of the tongues rest in the coupling direction of rotation (in FIG. 5, clockwise), while in the reverse direction, pinion 58 can rotate freely relative to cocking element 33.

By means of the rotation of the cocking element 33, the drive spring 22 is tensioned. In this embodiment, the drive spring 22 is formed as a spiral spring and is located in a recess 64 of the rotatably moveable cocking element 33 facing the drive rotor 24.

In this embodiment, the output-side coupling mechanism 25 again includes a control curve 27, which is formed by a recess 29 in drive rotor 24. The control curve 27 has, in the case shown, the shape of a circle eccentric to the axis C. During rotation of the drive rotor 24 a control pin 28 (FIG. 8), which is a component of a lancet holder 65, travels along recess 29. For fixing of a lancet (not shown), the lancet holder 65 has elastic arms 66 and a stop element 67, whose shape is adapted to the corresponding shape of a lancet, such that the latter is held in a reproducible longitudinal position in the holder 65. This design principle is known (for example, from U.S. Pat. No. 5,318,584) and need not be explained in more detail.

The rear end of lancet holder 65 with control pin 28 engages in a circumferential gap of the drive module 55 in such a manner that rotational movement of the components of module 55 is not hindered. To this end the shown embodiment comprises a separating disc 68 made, for example, of metal, which lies on a plateau of the drive rotor 24 in such a manner that the circumferential gap remains. It has a width required for accommodating the lancet holder 65 between disc 68 and the parts of the rotor 24 that are radially outward from control curve 27.

In this embodiment, the cocking- and puncture movement again includes the phases explained with reference to FIGS. 1 through 3:

During cocking, the rotatably moveable cocking element 33 rotates in a specified direction (in FIG. 4, clockwise), whereby spring 22 is tensioned, while the rotation of the drive rotor 24 (by means of a release mechanism, not shown, acting on a locking pin 70 (FIG. 6)) is inhibited.

In a puncture phase, drive spring 22 drives drive rotor 24 (after release of the stoppage acting on the pin 70), while, at the same time, the cocking element 33 is arrested (for example, by means of an elastic catch, not shown, engaging in a recess of the cocking element 33) against a reverse rotation.

Based on the preceding description, numerous alternative embodiments of the invention are apparent to a person skilled in the art. For example, the following modifications can be made:

A translatory movable actuator element 36 (FIG. 1) can, of course, be designed in such a manner that the lancet drive is tensioned not by means of a forward movement of the actuator element (in the puncture direction 13), but rather by a reverse movement (that is, through pulling instead of pressing).

As a drive spring 22, basically each rotationally elastic spring element is suited. This includes, in particular, a torsion spring, or a torsion bar.

In the embodiment shown (FIG. 2), the inhibition of the drive rotor 24 is coupled with a manually operated release. Alternatively, however, it is possible to use a self-releasing inhibition, which releases the rotational movement of the drive rotor, when the torque transferred from the drive spring 22 to the drive rotor 24 exceeds a defined value. In combination with an actuator element that is translatory moveable in the puncture direction for the cocking movement, a lancet drive results, with which the entire movement process runs automatically upon pressing of the actuation element.

The foregoing description of the invention is illustrative only, and is not intended to limit the scope of the invention to the precise terms set forth. Although the invention has been described in detail with reference to certain illustrative embodiments, variations and modifications exist within the scope and spirit of the invention as described and defined in the following claims.

What is claimed is:

1. A blood removal system for removing blood for diagnostic purposes, comprising:
   a housing;
   a lancet drive connected to the housing and including:
      a drive spring;
      a cocking element connected to the drive spring;
      a drive rotor connected to the drive spring; and
      a coupling mechanism coupled to the drive rotor;
   wherein:
      during a cocking phase of the lancet drive the cocking element rotates in a first direction to tension the drive spring while the drive rotor is inhibited from rotating in the first direction;
      during a driving phase of the lancet drive the drive rotor is rotatably driven in the first direction while the cocking element is arrested against a backward rotation, the coupling mechanism converting rotational movement of the drive rotor to movement of the lancet along a puncture path; and
      a 360° rotation of the drive rotor causes a single puncture and return movement of the lancet.

2. The blood removal system of claim 1, wherein the cocking element rotates about a first axis, and the drive rotor rotates about a second axis substantially parallel to the first axis.

3. The blood removal system of claim 2, wherein the first axis is coaxial to the second axis.

4. The blood removal system of claim 1, further including a rotatable actuation element coupled to the cocking element.

5. The blood removal system of claim 1, further including a transmission coupled to the cocking element, the transmission having a translatory movable actuation element.

6. The blood removal system of claim 1, wherein the cocking element rotates about a first axis.

7. The blood removal system of claim 6, further including a translatory movable actuation element that is movable in an actuation direction, the first axis being transverse to the actuation direction.

8. The blood removal system of claim 7, wherein the actuation element includes a gear rod and a pinion gear that is coupled to the cocking element during the cocking movement.

9. The blood removal system of claim 8, wherein the pinion gear, the cocking element, and the drive rotor are components of a drive module.

10. The blood removal system of claim 9, wherein the drive rotor includes a recess and the drive module further includes a control pin that travels along the recess as the drive rotor rotates during the drive phase, thereby determining at least a part of the puncture and return movement of the lancet, the recess being formed on a side of the drive rotor facing the cocking element.

11. The blood removal system of claim 9, wherein the pinion gear, the cocking element, and the drive rotor rotate about a common axis.

12. The blood removal system of claim 1, wherein the drive rotor moves through an angle of rotation range including a preparation range during which the drive rotor rotates at a first speed and a puncture range during which the drive rotor rotates at a second speed that is faster than the first speed.

13. The blood removal system of claim 12, wherein drive rotor rotation is inhibited at a transition in the angle of rotation range between the preparation range and the puncture range such that upon further rotation of the cocking element, the drive spring is tensioned.

14. The blood removal system of claim 1, further including a pawl configured to inhibit drive rotor rotation, and a release coupled to the pawl configured to permit drive rotor rotation.

15. The blood removal system of claim 1, wherein the drive rotor is automatically released to permit drive rotor rotation when the drive spring is tensioned to a tensioned state.

16. The blood removal system of claim 1, wherein the coupling mechanism includes a recess and a control pin engaging the recess.

17. The blood removal system of claim 16, wherein the control pin travels along the recess as the drive rotor rotates during the drive phase, thereby determining at least a part of the puncture and return movement of the lancet.

18. The blood removal system of claim 16, wherein a maximum displacement of the lancet in the puncturing direction is determined by a lower reversal point of a control curve defined by the recess.

19. The blood removal system of claim 16, wherein the recess is formed in the drive rotor.

20. The blood removal system of claim 1, wherein the lancet moves in the housing along a predetermined puncture path.

21. The blood removal system of claim further including a lancet guide connected to the housing, the lancet guide being configured to guide the lancet along the puncture path.

22. The blood removal system of claim 1, wherein the coupling mechanism includes a pushrod having a holding element configured to couple with the lancet.

23. The blood removal system of claim 1, wherein the coupling mechanism includes a rotatable element coupled to the drive rotor and a driving sleeve, the rotatable element having a control curve formed on an outer surface, and the driving sleeve having a control pin configured to travel within the control curve as the rotatable element rotates with rotation of the drive rotor.

24. The blood removal system of claim 23, wherein the drive sleeve moves within the housing along a puncturing axis as the drive rotor rotates in the first direction.

25. The blood removal system of claim 23, wherein the lancet reaches a position of maximum penetration when the control pin reaches a lower reversal point along the control curve.

26. The blood removal system of claim 1, wherein the drive spring encircles a portion of the drive rotor.

27. The blood removal system of claim 1, wherein the cocking element is coupled to a shaft having a control curve formed on an outer surface.

28. The blood removal system of claim 27, further including an actuator element having a control pin, the actuator element being configured to move along a puncturing axis during the cocking movement such that the control pin travels within the shaft control curve, thereby causing the shaft and the cocking element to rotate in the first direction.

29. The blood removal system of claim 28, wherein the actuator element moves away from the housing exit opening during the cocking movement.

30. The blood removal system of claim 1, further including a locking cam having a first catch and a second catch, the drive rotor including a stop element that engages the first catch during the cocking movement, thereby inhibiting drive rotor rotation.

31. The blood removal system of claim 30, wherein the locking cam is pivotally mounted within the housing for movement between a first position wherein the first catch engages the stop element and a second position wherein the first catch disengages the stop element, thereby permitting drive rotor rotation.

32. The blood removal system of claim 31, wherein the stop element engages the second catch after the drive phase.

33. The blood removal system of claim 31, wherein the locking cam is movable to a third position when the second catch disengages the stop element, thereby permitting a preparation angle of drive rotor rotation after which the stop element engages the first catch.

34. The blood removal system of claim 33, wherein the coupling mechanism couples to the lancet as the drive rotor rotates through the preparation angle of drive rotor rotation.

35. The blood removal system of claim 33, wherein the lancet drive is configured to eject a used lancet as the drive rotor rotates through the preparation angle of drive rotor rotation.

36. The blood removal system of claim 1, wherein the cocking element and drive rotor rotate about a first axis that is substantially perpendicular to a puncturing axis.

37. The blood removal system of claim 36, further including a pinion coupled to the cocking element and an actuator element having a gear rod, wherein the gear rod engages the pinion as the actuator element is moved along the puncturing axis, thereby causing the pinion and the cocking element to rotate about the first axis.

38. The blood removal system of claim 36, wherein the cocking element includes a first recess substantially opposite the drive rotor and a second recess facing the drive rotor.

39. The blood removal system of claim 38, wherein the drive spring is positioned substantially within the second recess.

40. The blood removal system of claim 38, further including a free wheel connected to the pinion and positioned substantially within the first recess.

41. The blood removal system of claim 40, wherein the free wheel includes an elastic tongue that engages a stop of the cocking element to facilitate simultaneous movement of the pinion and the cocking element in the first direction about the first axis during the cocking movement, and disengages the stop to permit movement of the pinion relative to the cocking element in the opposite direction.

42. The blood removal system of claim 36, wherein the drive rotor includes a substantially circular control curve that is eccentrically located relative to the first axis.

43. The blood removal system of claim 42, further including a lancet holder configured to receive the lancet, the lancet holder including a control pin and being movably positioned within the housing such that the control pin travels within the drive rotor control curve as the drive rotor rotates about the first axis.

44. The blood removal system of claim 42, further including a separating disc positioned between the drive rotor and the spring, the separating disc forming a gap for receiving a portion of the lancet holder.

45. The blood removal system of claim 1, wherein the drive rotor moves through an angle of rotation range including a preparation range during which the drive rotor rotates at a first speed and a puncture range during which the drive rotor rotates at a second speed that is different than the first speed.

46. A blood removal system for removing blood for diagnostic purposes, comprising:
a housing;
a lancet drive connected to the housing and comprising:
a drive spring;
a cocking element connected to the drive spring;
a drive rotor connected to the drive spring; and
a coupling mechanism coupled to the drive rotor;
wherein:
during a cocking phase of the lancet drive the cocking element rotates in a first direction to tension the drive spring while the drive rotor is inhibited from rotating in the first direction;
during a driving phase of the lancet drive the drive rotor is rotatably driven in the first direction while the cocking element is arrested against a backward rotation, the coupling mechanism converting rotational movement of the drive rotor to movement of the lancet along a puncture path; and
the coupling mechanism comprises a control curve and a control pin which travels along the control curve during the drive phase, thereby determining at least a part of the puncture path.

47. The blood removal system of claim 46, wherein the control curve is located in the drive rotor.

48. The blood removal system of claim 46, wherein the cocking element is coupled by a transmission to a translatory movable actuation element.

49. A blood removal system for removing blood for diagnostic purposes, comprising:
a housing;
a lancet drive connected to the housing and comprising:
a drive spring;
a cocking element connected to the drive spring;
a drive rotor connected to the drive spring; and
a coupling mechanism coupled to the drive rotor;
wherein:
during a cocking phase of the lancet drive the cocking element rotates in a first direction to tension the drive spring while the drive rotor is inhibited from rotating in the first direction;
during a driving phase of the lancet drive the drive rotor is rotatably driven in the first direction while the cocking element is arrested against a backward rotation, the coupling mechanism converting rotational movement of the drive rotor to movement of the lancet along a puncture path; and the cocking element is coupled by a transmission to a translatory movable actuation element.

50. The blood removal system of claim 49, wherein the axis of rotation of the cocking element is transverse to the direction of movement of the actuation element.

51. The blood removal system of claim 50, wherein the actuation element comprises a gear rod on a pinion gear that is coupled with the cocking element during the cocking phase of the lancet drive.

52. The blood removal system of claim 51, wherein the pinion gear, the cocking element and the drive rotor are components of a drive module and are rotatable about a common axis.

53. The blood removal system of claim 49, wherein the axis of rotation of the drive rotor is perpendicular to the direction of the puncture path.

54. A blood removal system for removing blood for diagnostic purposes, comprising:
a housing;
a lancet drive connected to the housing and comprising:
a drive spring;
a cocking element connected to the drive spring;
a drive rotor connected to the drive spring; and
a coupling mechanism coupled to the drive rotor;
wherein:
during a cocking phase of the lancet drive the cocking element rotates in a first direction to tension the drive spring while the drive rotor is inhibited from rotating in the first direction;
during a driving phase of the lancet drive the drive rotor is rotatably driven in the first direction while the cocking element is arrested against a backward rotation, the coupling mechanism converting rotational movement of the drive rotor to movement of the lancet along a puncture path; and
the axis of rotation of the drive rotor is perpendicular to the direction of the puncture path.

55. The blood removal system of claim 54, wherein the axis of rotation of the cocking element is parallel or coaxial to the axis of rotation of the drive rotor.

56. The blood removal system of claim 55, wherein the cocking element and the drive rotor are components of a drive module and are rotatable about a common axis.

57. The blood removal system of claim 56, wherein the drive spring comprises a spiral spring located in the drive module.

58. The blood removal system of claim 54, wherein the drive rotor rotates through a preparation angle of rotation range at a first speed and rotates through a puncture angle of rotation range at a second speed that is faster than the first speed.

59. A blood removal system for removing blood for diagnostic purposes, comprising:
a housing;
a lancet drive connected to the housing and comprising:
a drive spring;
a cocking element connected to the drive spring;
a drive rotor connected to the drive spring; and
a coupling mechanism coupled to the drive rotor;
wherein:
during a cocking phase of the lancet drive the cocking element rotates in a first direction to tension the drive spring while the drive rotor is inhibited from rotating in the first direction:
during a driving phase of the lancet drive the drive rotor is rotatably driven in the first direction while the cocking element is arrested against a backward rotation, the coupling mechanism convening rotational movement of the drive rotor to movement of the lancet along a puncture path; and
the drive rotor rotates through a preparation angle of rotation range at a first speed and rotates through a puncture angle of rotation range at a second speed that is faster than the first speed.

60. The blood removal system of claim 59, wherein in the preparation angle of rotation range torque is transferred from the cocking element to the drive rotor by turning the cocking element.

61. The blood removal system of claim 59, wherein the rotational movement of the drive rotor is inhibited at a transition in the angle of rotation range between the preparation range and the puncture range such that the drive spring, upon further rotation of the cocking element, is tensioned far puncture movement.

62. The blood removal system according to claim 61, wherein the inhibition of the rotational movement of the drive rotor is provided by a pawl coupled with a release.

63. The blood removal system of claim 61, wherein the inhibition is self-releasing, wherein the drive rotor is released when the drive spring reaches a tensioned state required for the puncture movement.

64. The blood removal system of claim 61, comprising a lancet holder with elastic arms and a stop element, the elastic arms and the stop element having a shape corresponding to the shape of a lancet such that the lancet is held in the lancet holder in a reproducible longitudinal position.

* * * * *